United States Patent [19]

Shih

[11] Patent Number: 5,156,914
[45] Date of Patent: Oct. 20, 1992

[54] PROCESS FOR PRODUCING PARTICULATE SILICON ENCAPSULATED PRODUCTS

[75] Inventor: Jenn S. Shih, Paramus, N.J.

[73] Assignee: ISP Investments Inc., Wilmington, Del.

[21] Appl. No.: 696,475

[22] Filed: May 6, 1991

[51] Int. Cl.⁵ .......................... A61K 7/075; B01J 13/18
[52] U.S. Cl. ............................ 428/402.22; 252/315.1; 264/4.3; 264/4.33; 264/4.7; 424/70; 424/71; 507/902; 514/965; 525/936; 526/922
[58] Field of Search ......................... 264/4.3, 4.33, 4.7; 428/402.22; 525/936; 526/922; 514/965

[56] References Cited

U.S. PATENT DOCUMENTS

| | | | |
|---|---|---|---|
| 3,551,346 | 12/1970 | Breen et al. | 264/4.32 |
| 3,704,264 | 11/1972 | Gorman | 428/402.22 |
| 4,097,404 | 6/1978 | Brown | 264/4.7 |
| 4,677,003 | 6/1987 | Redlich et al. | 428/402.22 X |
| 4,798,691 | 1/1989 | Kasai et al. | 264/4.7 |
| 4,880,617 | 11/1989 | Chromcek et al. | 514/965 X |

FOREIGN PATENT DOCUMENTS

| | | | |
|---|---|---|---|
| 639730 | 4/1962 | Canada | 252/358 |
| 1025694 | 4/1966 | United Kingdom . | |

*Primary Examiner*—Richard D. Lovering
*Attorney, Agent, or Firm*—Marilyn J. Maue; Joshua J. Ward

[57] ABSTRACT

This invention relates to an anhydrous, liquid phase process for entrapping droplets of a silicon compound in an organic polymer which involves precharging a reactor at between about 50° and about 80° C. with a polymerization initiator and a non-polar solvent in which the silicon compound is soluble; adding to the precharged reactor, silicon compound under vigorous agitation and gradually introducing from about 50 to about 99 wt. %, based on silicon compound, of a polymerizably precipitatable, aliphatically unsaturated monomer at a controlled rate; continuously polymerizing the monomer component, under vigorous agitation with the silicon compound, at between about 50° and about 165° C. while maintaining a desired monomer level of not more than 10% in the reactor and recovering a solid particulate product of silicon droplets entrapped in said polymerized monomer.

24 Claims, No Drawings

PROCESS FOR PRODUCING PARTICULATE SILICON ENCAPSULATED PRODUCTS

In one aspect, this invention relates to a process for the preparation of a water-soluble or water-swellable silicon compound in a particulate form.

In another aspect, the invention relates to the fine powder product of the present process.

BACKGROUND OF THE INVENTION

Silicon fluids such as oils, gums and gels have been found to possess many beneficial properties such as thermal stability, oxygen permeability, lubricity and good surface release when applied as coatings. Accordingly, these compounds are desirable additives in many formulations such as commercial thickeners, cleaning solutions and cosmetic compositions. Notwithstanding their beneficial properties, however, these silicon compounds are generally immiscible with water, a factor which limits their use in commercially desirable aqueous dispersions. In such cases where silicons have been employed, it has been necessary to include relatively large amounts of a surfactant or surfactant mixture and, in some instances, a stabilizing agent, to overcome the low dispersability and water immiscibility of the silicon compound. The dilution effect of such surfactants and/or stabilizers significantly increases the cost, and in many cases degrades the quality, of the resulting formulation. Also, it has been found that, even with the use of a surfactant, the desired dispersion stability is often lacking. Therefore, it is an aim of research to provide a silicon compound in a water-soluble or water-swellable form, most desirably in a stable particulate state so as to facilitate shipping and handling.

Accordingly, it is an object of this invention to provide a novel silicon water-soluble or water-swellable powder.

Another object of this invention is to provide an economical and commercially feasible process for producing the desired silicon compound.

These and other objects of the invention will become apparent from the following description and disclosure.

THE INVENTION

In accordance with this invention there is provided a non-aqueous, liquid phase process for forming discrete particles, most desirably in powder form, of a silicon compound encapsulated in a water-soluble or water-swellable polymer, which process comprises precharging a reactor at between about 50° and about 80° C. with a polymerizing amount of a free radical initiator and a non-polar solvent in an amount sufficient to solubilize a selected silicon compound; adding to the precharged reactor, the silicon compound under vigorous agitation and gradually introducing from about 50 to about 99 wt. %, based on silicon compound, of a polymerizably precipitatable, aliphatically unsaturated monomer at a controlled rate; continuously polymerizing the monomer, under vigorous agitation with the silicon compound, at between about 50 and about 165° C. while maintaining a desired monomer level of not more than 10% in the reactor and recovering a solid particulate product of silicon droplets entrapped in said polymerized monomer by separation from the reaction mixture.

The order of addition as precharge is critical to the formation of polymeric particles; however, the silicon compound and the monomeric component can be introduced simultaneously or separately into the precharged reactor. When the monomeric component is introduced separately, it has been found beneficial, but not essential, to feed the monomer below the surface of the liquid reaction mixture containing dissolved silicon compound to promote better contact. Also, an excess of the monomeric component, e.g. from about 50 to about 99 wt. % based on the silicon compound, is preferred in the present process. The most desirable weight ratio of monomer to silicon compound is between about 4:1 and about 8:1.

The silicon compounds, primarily silanes, siloxanes and silanols, used in the present invention are those which are soluble in a non-polar organic solvent and are solids or non-volatile liquids having a viscosity of between about 5 and about 600,000 centistokes (cs) at 25° C. These include polyalkyl siloxanes, polyaryl siloxanes, hydroxylated and/or halogenated polyaryl- or polyalkyl- siloxanes, polyalkaryl siloxanes, polyether siloxane copolymers and alkylene acrylate* derivatives of polyalkyl-, polyaryl- or polyalkaryl- siloxanes as well as trialkyl silanols, silicon halides such as hexachloro polysilane, hexaaryl polysilanes and other silicon containing compounds having a boiling point greater than about 165° C., species of which are disclosed in U.S. Pat. Nos. 2,826,551; 3,964,500 and 4,364,837 as well as in British Pat. No. 849,433; all incorporated herein by reference.

* "Acrylate" or "acrylic" as used herein, is intended to include both unsubstituted acrylate and methacrylate or unsubstituted acrylic and methacrylic compounds.

Preferred of these silicon compounds are those having a viscosity of from about 100 to about 100,000 cs which are described by the formula

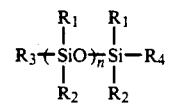

wherein n has a value of from 0 to 50, $R_1$, $R_2$, $R_3$ and $R_4$ are each individually hydrogen, chloro, bromo, hydroxyalkyl, lower alkyl or phenyl and wherein $R_3$ alternatively can be alkylene acrylate. These compounds can be employed individually, in admixtures or as silicon copolymers, for example, poly[(dimethylsiloxane)/(diphenylsiloxane)], and other combinations of the above designated species. Examples of these preferred silicon compounds include polydimethyl siloxanes, polymethylphenyl siloxanes, polymethylsilanols, tetramethylbis(chloromethyl) disiloxane, trimethyloxy silyl propyl methacrylate, trimethyloxy silyl methyl methacrylate etc. Of these, the polydimethylsiloxanes are most preferred.

The silicon solubilizing solvents employed herein include linear, branched or cyclic alkanes having from 2 to 20 carbon atoms; although cyclohexane and heptane are particularly recommended. The silicon compound is intimately mixed and disso dissolved in the selected solvent at a temperature of from about 50° to about 80° C. Generally the silicon solution formed in the reactor contains from about 0.5 to about 50%, preferably from about 0.5 to about 10%, of dissolved silicon compound.

The aliphatically unsaturated monomer employed in the present invention can be an individual monomeric compound or it can be a mixture of copolymerizable monomers which are soluble in the reaction mixture and which form a water-soluble or water-swellable precipitate when polymerized. These monomeric components include acrylic acids, acrylamide, N-vinylpyrrolidone, N-vinylcaprolactam, alone or in admixture with less than 50% of a comonomer such as a $C_1$ to $C_4$ alkyl acrylate, an acrylic acid, vinyl acetate, N,N-dimethylaminoethyl methacrylate, N,N-dimethylaminomethyl acrylate, N,N-dimethylaminopropyl methacrylate, N,N-dimethylaminopropyl methacrylamide, N,N-dimethylaminoethyl acrylamide or a crosslinking agent such as N,N-divinylimidazolidone, the divinyl ether of diethylene glycol, pentaerythritol triallyl ether, triallyl-1,3,5-triazine-2,4,6-(1H,3H,5H)trione, ethylene glycol diacrylate, 2,4,6-triallyloxy-1,3,5-triazine, 1,7-octadiene, 1,9-decadiene, divinyl benzene and methylene bis(acrylamide) or any other comonomer which is capable of forming with the primary monomer a macro- or microcellular polymeric structure around the silicon molecule.

Generally the monomer or monomeric mixture is introduced into the precharged reactor at a controlled rate, with high shear mixing over an extended period depending on the solvent employed. The reaction mixture requires vigorously agitation under an inert atmosphere, e.g. a nitrogen atmosphere, during polymerization. A stirring rate of from about 100 to about 800 rpm is generally adequate to keep the monomeric species uniformly distributed and the polymeric precipitate product dispersed throughout the polymerization reaction. In a preferred embodiment, the polymerization reaction is carried out in a low and a high temperature stage, i.e. the later stage of polymerization is effected at a higher temperature of between about 100° and about 165° C., most preferably between about 110° and about 130° C., as opposed to the formation of the silicon solution, and early stage of polymerization at 50° to 80° C., preferably at 60° to 70° C.

At the high temperature level, the monomer concentration in the reactor is controlled to below 2%, more desirably below 1%, as can be determined by iodine titration. Further, the precipitated solids level in the reaction should be maintained at between about 10% and about 50%, preferably between about 15% and about 30%.

When the entire reaction is carried out at a temperature below 100° C., with a low temperature initiator, the monomer concentration in the polymerizing mixture can be allowed to rise to about 10%, more desirably to about 6%.

These limits of monomer concentration are critical since it is discovered that monomer levels above 10% in the low temperature operation, or monomer levels at or above 2% in the high temperature operation produce non-particulate, gummy, gelatinous products which are difficult to handle and purify. Accordingly, the feed rate of the monomeric component is also critical to the success of the process and is controlled to between about 0.08 and about 2.5 g/minute/1000 g. of solvent. In preferred embodiments of the invention, N-vinyl pyrrolidone or cross-linking agent and N-vinyl pyrrolidone feed rate of from about 0.8 to about 1.3 g/minute/1000 g. of cyclohexane or from about 0.3 to about 0.8 g/minute/1000 g. of heptane, are employed to obtain a particulate product in fine powdery form.

The monomeric component is introduced over a period of from about 2 to about 15 hours in order to achieve a desired high polymer solids level in the reactor, e.g. between 10 and 50% solids, preferably between 15 and about 30% solids.

The polymerization initiator of in the present reaction, which is precharged to the reactor at a temperature of between about 50° and about 80° C., is a low temperature, free radical initiator or, when the reaction is partially conducted at 100° C. or above, can be a mixture of low and high temperature initiators, employed in catalytic amount, for example, between about 0.2 and about 15%, preferably between about 1 and about 5%, based on the weight of total monomer charged. Suitable low temperature initiators are represented by the free-radical polymerization inducing peroxides such as hydrogen peroxide, diacyl peroxides such as diacetyl peroxide, dibenzoyl peroxide, dilauroyl peroxide; peresters such as t-butylperoxy pivalate, t-butyl peroctoate, t-amylperoxy pivalate, t-butylperoxy-2-ethyl hexanolate; percarbonates such as dicyclo hexyl peroxy dicarbonate, as well as azo compounds such as 2,21'-azo-bis(isobutylronitrile), 2,21'-azo-bis(2,4-dimethylvaleronitile), 2,21'-azo-bis(cycanocyclohexane). However, the organic peroxides are more desirably recommended.

Preferred operation involves continuously metering the initiator or introducing the initiator at several stages or intermittently during the polymerization reaction. However, when the temperature of the reaction is raised to 100° C. and above, high temperature initiators, having a half life of at least 10 hours at 100° C. or above, are employed. Representative examples of these high temperature initiators include, 2,5-dimethyl-2,5-di-(t-butylperoxy) hexane, di-t-butyl peroxide, dicumyl peroxide, t-butylcumyl peroxide, t-butylperoxy maleic acid, t-butyl hydroperoxide, 2,2-di(t-butylperoxy) butane, ethyl-3,3-di(t-butylperoxy) butyrate, t-butyl peroxy acetate, t-butylperoxy benzoate and the like. Thus, in the preferred operation, the reactor is precharged with a low temperature initiator, the silicon and monomer(s) are introduced and polymerization takes place at a temperature of between about 50° and about 80° C., e.g. 60°–70° C. Subsequently, e.g. after about 2 hours or more, the reaction temperature is raised to 100° C. or above, most preferably to 110°–30° C. and a high temperature initiator is introduced at one or more stages, to complete the reaction. It has been found that at the higher temperatures, above about 100° C., products containing substantially less than 2%, usually less than 1% monomer are produced. Also, the gradual or intermittent introduction of initiators throughout the polymerization reaction insures high conversion of monomer.

The present reaction is carried out under a pressure ranging from about atmospheric to about 80 psig with thorough mixing until the desired amount of polymeric precipitate has been formed. Because of the vigorous mixing and the controlled feed rate of monomeric component, a polymeric film is formed around a molecule of the silicon compound so as to entrap droplets of the silicon within the particulate polymeric structure. Of course, it is understood that during the reaction, some molecules of the silicon may adhere to the external surface of the polymeric structure as well. This effect may take place when larger amounts of the silicon component are employed. However, such occasional attachment does not detract from the water solubility or water-swellability of the polymeric portion of the particulate product.

After the reaction is completed, the solids are removed from the reactor and recovered by filtration, decantation or by any other convenient means and the recovered solids are dried to produce discrete white particles, which, in most cases, have an average particle diameter of from about 40 to about 450 micrometers. The particulate product of this invention contains between about 1 and about 50%, preferably between about 10 and about 20% silicon compound, depending upon the feed ratio of the silicon to monomeric component.

The products of the present invention combine the valuable properties of both the silicon compound and the polymeric encapsulating agent, which properties include flexibility, hair and skin substantivity, thermal stability, oxygen permeability, etc. as well as providing glossy, lustrous coatings having excellent release properties.

The use of the present products in hair formulations such as shampoos, conditioners, hair dyes or bleaches, hair structure altering compositions, is particularly desirable for their lusterous effects. Generally, between about 8 and about 30 wt. %, preferably between about 10 and about 20 wt. %, of non-crosslinked polymer and between about 0.5 and about 10%; preferably between about 1 and about 8%, of crosslinked polymer imparts high gloss when incorporated into a standard hair or skin formulation, particularly a shampoo or conditioning formulation. These formulations, of course, may also include other adjuvants such as perfumes, essential oils, dyes and the like to enhance commercial acceptability. A typical lusterizing shampoo composition may contain the following components.

|  | Wt. % | |
|---|---|---|
| Silicon in Crosslinked Polymer | 5 | — |
| Silicon in Non-Crosslinked Polymer | — | 18 |
| Hair bodying component | — | 5 |
| Suds booster | 2 | 2 |
| Ethanol | 20 | 18 |
| Water | 45 | 40 |
| Amphoteric detergent | 25 | 20 |
| Perfume, colorant, UV Absorber | QS | QS |

Another use for the present products is in the field of commercial thickeners which are added to compositions in oil recovery, textiles and detergents.

Having thus described the invention, reference is now had to the accompanying examples which illustrate preferred embodiments but which are not to be construed as limiting to the scope of the invention as more broadly defined above and in the appended claims.

EXAMPLE 1

In a 2 liter, four-necked reaction kettle equipped with a condenser, a constant speed (set at 170 rpm) mechanical stirrer with torque reading and anchor agitator (open radius=4 and 5/6 inches), two dip tubes connected to two separate metering pumps, a nitrogen purge adaptor; and a thermocouple connected to the temperature controller, 1000 grams of cyclohexane were charged and the reactor was heated to 65° C. in 30 minutes with nitrogen purge throughout the entire process. The reactor was held at 65° C. for 30 minutes, after which 520 microliters of t-butylperoxy pivalate (Lupersol 11) was added followed by addition of a solution of 250 grams of vinylpyrrolidone (VP), 1.25 grams of pentaerythritol triallyl ether crosslinking agent and 25 grams of silanol terminated polydimethyl siloxane were added to the reactor over a period of 4 hours at a rate of 1-1.1 ml/minute). After completion of the addition, the resulting mixture was stirred at 65° C. overnight and thereafter heated to 85° C. for 1 hour after which t-butylperoxide pivalate (200 microliters) were charged each hour for an additional 4 hours at 85° C. to complete the reaction. The reaction mixture was then cooled to room temperature, after which it was dried in an oven at 100° C. for 16 hours and then in a vaccum oven at 90° C. for an additional 16 hours, whereupon 98% yield of a white powdery product in which at least 80% of the silicone compound was entrapped in a cross-linked polyvinylpyrrolidone matrix is recovered.

EXAMPLE 2

Example 1 was repeated, except that 1000 g. of heptane was substituted for 1000 g. of cyclohexane; 1.25 g of divinyl imidazolidone crosslinking agent and a feed rate of 0.5-0.55 ml/minute was substituted for pentaerythritol triethyl ether and a feed rate of 1-1.1 ml/minute.

The product of this example was recovered in 98% yield as a white powder in which at least 80% of the silicone compound was encapsulated in the crosslinked polyvinylpyrrolidone matrix.

EXAMPLE 3

In a 2 liter, four-necked reaction kettle equipped with a condenser, a constant speed (set at 170 rpm) mechanical stirrer with torque reading and anchor agitator (open radius=4 and 5/6 inches), two dip tubes connected to two separate metering pumps, a nitrogen purge adaptor, and a thermocouple connected to the temperature controller, 1000 grams of cyclohexane were charged and the reactor was heated to 65° C. in 30 minutes with nitrogen purge throughout the entire process. The reactor was held at 65° C. for 30 minutes, after which 520 microliters of t-butylperoxy pivalate (Lupersol 11) was added followed by addition of a solution of 250 grams of vinylpyrrolidone and 75 grams of Dow Corning 200 silicone fluid of 200 cs viscosity* were added to the reactor over a period of 4 hours at a rate of 1-1.1 ml/minute). After completion of the addition, the resulting mixture was stirred at 65° C. overnight and thereafter heated to 85° C. for 1 hour after which t-butylperoxide pivalate (200 microliters) were charged each hour for an additional 4 hours at 85° C. to complete the reaction. The reaction mixture was then cooled to room temperature, after which it was dried in an oven at 100° C. for 16 hours and then in a vaccum oven at 90° C. for an additional 16 hours, whereupon 94% yield of a white powdery product in which at least 90% of the silicone compound was entrapped in the non-crosslinked polyvinylpyrrolidone matrix is recovered.
* DC 200 polydimethyl siloxane

EXAMPLE 4

Example 3 was repeated except that 150 g of DC 200 was substituted for 75 g. of DC 200. The identical silicone encapsulated product was recovered in 92% yield.

EXAMPLE 5

Example 3 was repeated except that 25 g. of silanol terminated polydimethylsiloxane was substituted for 75 g. of DC 200. The identical silicone encapsulated product was recovered in 90% yield.

EXAMPLE 6

Example 3 was repeated except that 1000 g. of heptane was substituted for 1000 g. of cyclohexane, a feed rate of 0.5–0.55 ml/minute for VP and DC 200 was used instead of 1–1.1 ml/minute. The identical silicone encapsulated product was recovered in 96% yield.

EXAMPLE 7

In a 2 liter, four-necked reaction kettle equipped with a condenser, a constant speed (set at 170 rpm) mechanical stirrer with torque reading and anchor agitator (open radius=4 and 5/6 inches), two dip tubes connected to two separate metering pumps, a nitrogen purge adaptor, and a thermocouple connected to the temperature controller, 1000 grams of heptane were charged and the reactor was heated to 65° C. in 30 minutes with nitrogen purge throughout the entire process. The reactor was held at 65° C. for 30 minutes, after which 520 microliters of t-butylperoxy pivalate (Lupersol 11) was added followed by addition of a solution of 250 grams of N-vinyl caprolactam and 50 g. of monomethacryloxypropyl terminated polydimethylsiloxane over a period of 3 hours at a rate of 1.5 ml/minute). After completion of the addition, the resulting mixture was stirred at 65° C. overnight and thereafter heated to 85° C. for 1 hour after which t-butylperoxide pivalate (200 microliters) were charged each hour for an additional 4 hours at 85° C. to complete the reaction. The reaction mixture was then cooled to room temperature, after which it was dried in an oven at 100° C. for 16 hours and then in a vaccum oven at 90° C. for an additional 16 hours, whereupon 92% yield of a white powdery product in which at least 80% of the silicone product was entrapped in a non-crosslinked polyvinyl caprolactam matrix is recovered.

EXAMPLE 8

In a 2 liter, four-necked reaction kettle equipped with a condenser, a constant speed (set at 170 rpm) mechanical stirrer with torque reading and anchor agitator (open radius of 4 and 5/6 inches), two dip tubes connected to two separate metering pumps, a nitrogen purge adaptor, and a thermocouple connected to the temperature controller, 1000 grams of heptane were charged and the reactor was heated to 65° C. in 30 minutes with nitrogen purge throughout the entire process. The reactor was held at 65° C. for 30 minutes, after which 520 microliters of t-butylperoctate was added followed by addition of a solution of 250 grams of N-vinyl pyrrolidone and 50 g. of monomethacryloxypropyl terminated polydimethylsiloxane over a period of 7 hours at a rate of 0.6 ml/minute). After completion of the addition, the solution was transferred to a 2 liter stainless steel high pressure reactor and 1 gram of 2,5-dimethyl-2,5-di(t-butylperoxy) hexane added. The resulting mixture was then heated to 130° C. under 50 psi: within 1 hour and held at that temperature for 8 hours with constant agitation. The reaction mixture was then cooled to room temperature and the reactor contents transferred to an oven wherein it is dried at 100° C. for 16 hours and then in a vaccum oven at 90° C. for an additional 16 hours, whereupon a white powdery product containing less than 0 1% monomer and in which at least 80% of the silicone compound was entrapped in a non-crosslinked polyvinyl pyrrolidone matrix is recovered.

EXAMPLE 9

In a 2 liter, four-necked reaction kettle equipped with a condenser, a constant speed (set at 170 rpm) mechanical stirrer with torque reading and anchor agitator (open radius=4 and 5/6 inches), one dip tube connected to a separate metering pump, a nitrogen purge adaptor, and a thermocouple connected to the temperature controller, 1000 grams of heptane and 20 g. of monomethacryloxypropyl terminated polydimethylsiloxane were charged and the reactor was heated to 65° C. in 30 minutes with nitrogen purge throughout the entire process. The reactor was held at 65° C. for 30 minutes, after which 520 microliters of t-butylperoxy pivalate (Lupersol 11) was added followed by addition of a solution of 280 grams of N-vinyl caprolactam was introduced over a period of 3 hours at a rate of 1.5 ml/minute). After completion of the addition, the resulting mixture was stirred at 65° C. overnight and thereafter heated to 85° C. for 1 hour after which t-butylperoxy pivalate (200 microliters) were charged each hour for an additional 4 hours at 85° C. to complete the reaction. The reaction mixture was then cooled to room temperature, after which it was dried in an oven at 100° C. for 16 hours and then in a vaccum oven at 90° C. for an additional 16 hours, whereupon 95% yield of a white powdery product in which at least 85% of the silicone product was entrapped in a non-crosslinked polyvinyl caprolactam matrix, is recovered.

While the invention has been described with particular reference to certain embodiments, it is to be understood that many substitutions, alterations and modifications can be made therein which are also considered to be within the scope of this invention.

What is claimed is:

1. A liquid phase process for encapsulating silicone droplets in a water soluble or water swellable polymer under anhydrous, oxygen free conditions comprising
   (a) precharging a reactor with a reaction solvating amount of a non-polar hydrocarbon solvent and an effective polymerization promoting amount of a free radical polymerization initiator at a temperature of from about 50° to about 80° C.;
   (b) feeding to said precharged reactor a silicon compound which is soluble in said solvent and gradually introducing to said reactor, at a rate of from about 0.08 to about 2.5 g/minute/1000 g of solvent with vigorous agitation, between about 50 and about 99 wt. %, based on said silicon compound, of a polymerizably precipitatable, aliphatically unsaturated monomer;
   (c) continuously polymerizing said monomer optionally with introduction of additional amounts of initiator and precipitating polymer under vigorous agitation with said silicon compound at a temperature of from about 50° to about 165° C. wile maintaining the precipitated solids level at between about 10% and about 50% and the monomer level below about 10% in the reactor;
   (d) separating precipitated polymer containing entrapped silicon compound droplets from the reaction mixture and
   (e) drying said precipitate to a particulate product.

2. The process of claim 1 wherein said silicon compound has the formula

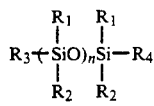

wherein n has a value of from 0 to 50, $R_1$, $R_2$, $R_3$ and $R_4$ are each individually hydrogen, chloro, hydroxyalkyl, lower alkyl or phenyl and $R_3$ can also be an alkylene acrylate.

3. The process of claim 1 wherein said monomer is selected from the group of acrylic acid, acrylamide, N-vinyl pyrrolidone, N-vinyl caprolactam and mixtures of N-vinyl pyrrolidone and N-vinyl caprolactam.

4. The process of claim 1 wherein said monomer is selected from the group of acrylic acid, acrylamide, N-vinylpyrrolidone, N-vinyl caprolactam, and mixtures of N-vinylpyrrolidone and/or N-vinyl caprolactam with a polyfunctional polymerizable comonomer.

5. The process of claim 4 wherein said comonomer is selected from the group of an acrylic acid, vinyl acetate, a $C_1$ to $C_4$ alkyl acrylate, N,N-dimethylaminoethyl methacrylate, N,N-dimethylaminomethyl acrylate, and N,N-dimethylaminopropyl methacrylate.

6. The process of claim 4 wherein the polyfunctional comonomer is a crosslinking agent selected from the group of triallyl-1,3,5-triazine-2,4,6-(1H,3H,5H)trione, N,N-divinyl-2-imidazolidone, the divinyl ether of diethylene glycol, 2,4,6-triallyloxy-1,3,5-triazine, ethylene glycol diacrylate, 1,7-octadiene, divinyl benzene, 1,9-decadiene, methylene bis(acrylamide) and pentaerythritol triallyl ether.

7. The process of claim 1 wherein said solvent is $C_2$ to $C_{20}$ alkane.

8. The process of claim 7 wherein said alkane is cyclohexane.

9. The process of claim 8 wherein said monomer is N-vinyl pyrrolidone optionally containing less than 50% cross-linking agent and the monomer is fed to said precharged reactor at a rate of from about 0.8 to about 1.3 g/minute/1000 g. of said cyclohexane.

10. The process of claim 7 wherein said alkane is heptane.

11. The process of claim 10 wherein said monomer is N-vinyl pyrrolidone optionally containing less than 50% cross-linking agent and the monomer is fed to said precharged reactor at a rate of from about 0.3 to about 0.8 g/minute/1000 g. of said heptane.

12. The process of claim 1 wherein the entire reaction is carried out at a temperature below 100° C. in the presence of a low temperature free-radical peroxide initiator and the monomer concentration in the reactor is maintained below 6%.

13. The process of claim 12 wherein between about 0.2 and about 5 wt. % based on monomer of the low temperature initiator is added continuously or in increments to the reaction mixture.

14. The process of claim 1 wherein an initial stage of the polymerization reaction is carried out at a temperature of between about 60° and 70° C. in the presence of a low temperature initiator and a final stage of the polymerization reaction is carried out at a temperature of between about 110° and about 130° C. in the presence of a high temperature free-radical peroxide initiator, having a 10 hour half life at 100° C. or above, and the monomer concentration in the reactor is maintained below 2%.

15. The process of claim 14 wherein the residual monomer in the reactor is maintained below 1%.

16. The process of claim 14 wherein between about 0.2 and about 5 wt. % based on monomer of the low temperature initiator is introduced gradually or at a plurality of stage during the low temperature polymerization.

17. The process of claim 14 wherein between about 0.3 and about 1 wt. % based on monomer of the high temperature initiator is introduced to the high temperature polymerization reaction.

18. The process of claim 1 wherein the concentration of silicon compound in said solvent is between about 0.5 and about 10 wt. %.

19. The process of claim 1 wherein the wt. % of silicon compound with respect to monomer is between about 1 and about 50%.

20. The process of claim 19 wherein said wt. % of silicon compound is between about 5 and about 30%.

21. The product of claim 3 which is a white powder containing 10–20% silicon compound.

22. The product of claim 21 wherein said silicon compound droplet is encapsulated in a non-crosslinked N-vinylpyrrolidone homopolymeric structure.

23. The product of claim 4 which is a white powder containing 10–20% silicon compound.

24. The product of claim 23 wherein said silicon compound droplet is encapsulated in a cross-linked N-vinylpyrrolidone structure.

* * * * *